United States Patent
Chesnin et al.

(10) Patent No.: US 8,535,244 B2
(45) Date of Patent: Sep. 17, 2013

(54) GUIDEWIRE AND METHOD OF INSERTION OF SAME

(75) Inventors: Kenneth J. Chesnin, Irvine, CA (US); Michael Basta, Kulpsville, PA (US); Sam Engle, Collegeville, PA (US); Michael Cellini, Phoenixville, PA (US); Kevin Sanford, Chalfont, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/839,108

(22) Filed: Jul. 19, 2010

(65) Prior Publication Data

US 2011/0015617 A1    Jan. 20, 2011

Related U.S. Application Data

(60) Provisional application No. 61/226,428, filed on Jul. 17, 2009.

(51) Int. Cl.
*A61M 25/00* (2006.01)

(52) U.S. Cl.
USPC .......................................... 600/585; 604/528

(58) Field of Classification Search
USPC . 600/433, 434, 585; 128/898; 606/191–196; 604/164.13
See application file for complete search history.

(56) References Cited

U.S. PATENT DOCUMENTS

| | | | | |
|---|---|---|---|---|
| 5,234,002 A | * | 8/1993 | Chan | 600/585 |
| 5,402,799 A | | 4/1995 | Colon et al. | |
| 5,978,699 A | * | 11/1999 | Fehse et al. | 600/585 |
| 6,190,333 B1 | * | 2/2001 | Valencia | 600/585 |
| 6,383,146 B1 | | 5/2002 | Klint | |
| 6,733,500 B2 | * | 5/2004 | Kelley et al. | 606/41 |
| 2004/0249349 A1 | | 12/2004 | Wentling | |
| 2006/0253048 A1 | * | 11/2006 | Jones et al. | 600/585 |
| 2007/0185446 A1 | * | 8/2007 | Accisano | 604/104 |
| 2009/0318881 A1 | * | 12/2009 | Shennib | 604/250 |

FOREIGN PATENT DOCUMENTS

WO        WO0048663        8/2000

OTHER PUBLICATIONS

International Search Report and Written Opinion; International Application No. PCT/US2010/042459; International Filing Date Jul. 19, 2010; 9 pages.
International Application No. PCT/US2010/042459, International Preliminary Report on Patentability, dated Jan. 17, 2012, 6 pages.

\* cited by examiner

*Primary Examiner* — Max Hindenburg
*Assistant Examiner* — Jonathan M Foreman
(74) *Attorney, Agent, or Firm* — Blank Rome LLP

(57) ABSTRACT

This invention provides a guidewire adapted for the catheterization of very small vasculature of the neonates, infants and children. In one embodiment of the invention, a guidewire of 0.010 inch diameter is described. The present invention also provides an alignment adaptor that facilitates catheterization of small vasculature utilizing said guidewire, and method of using the same.

10 Claims, 5 Drawing Sheets

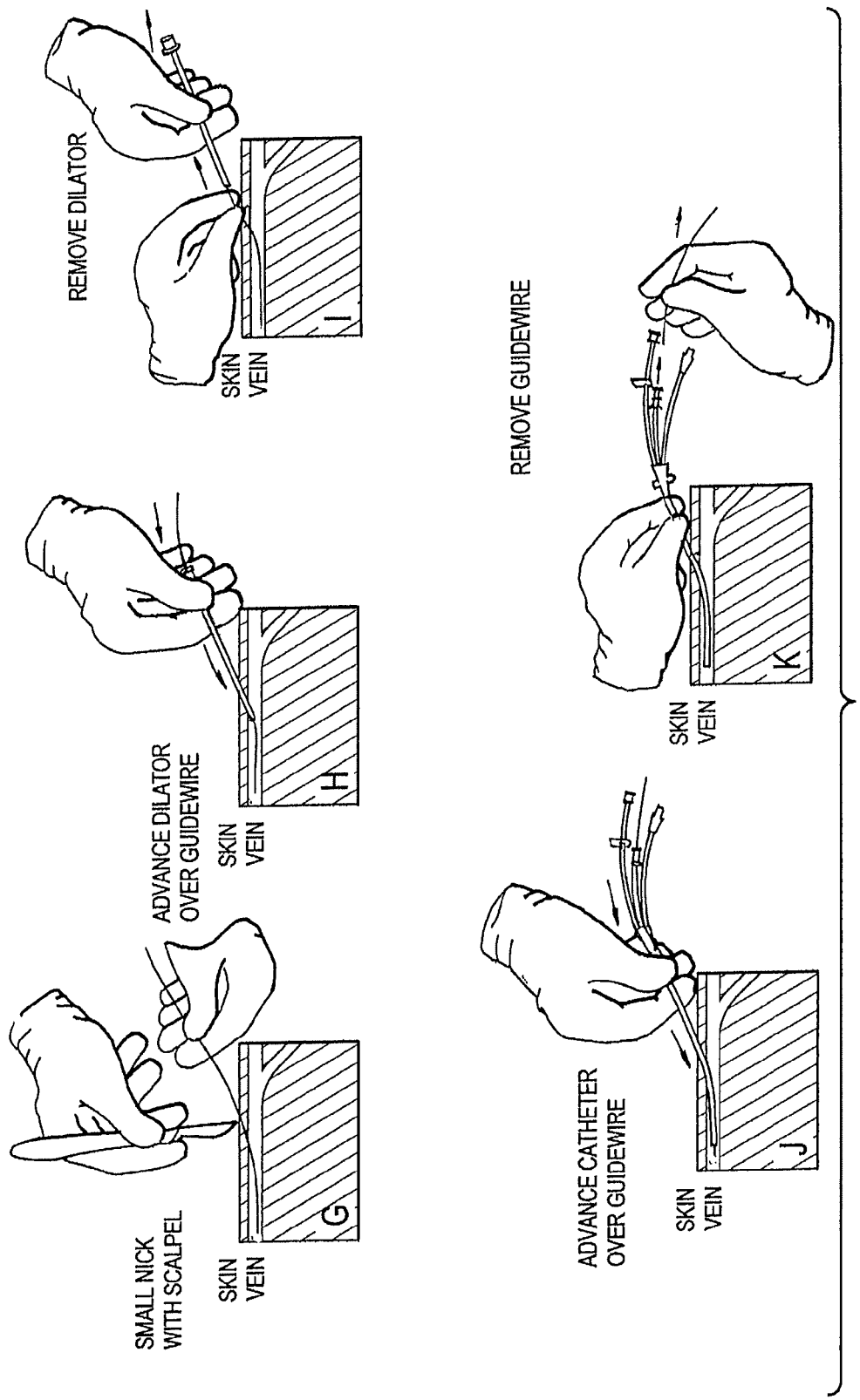

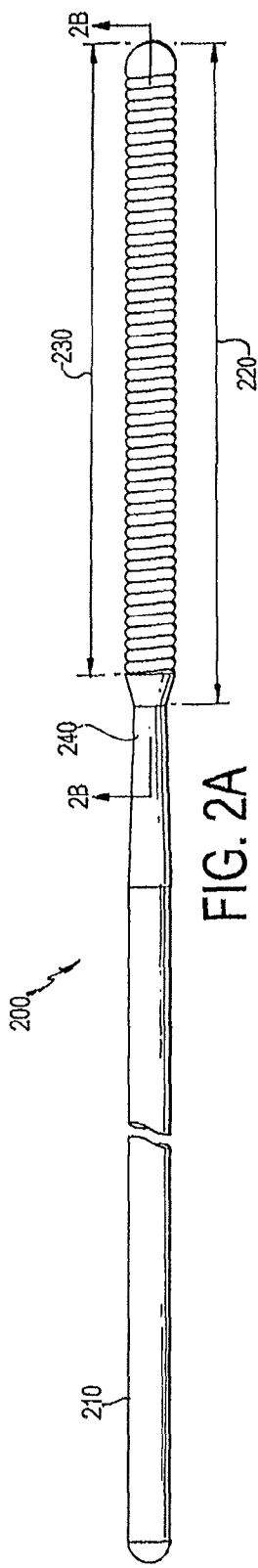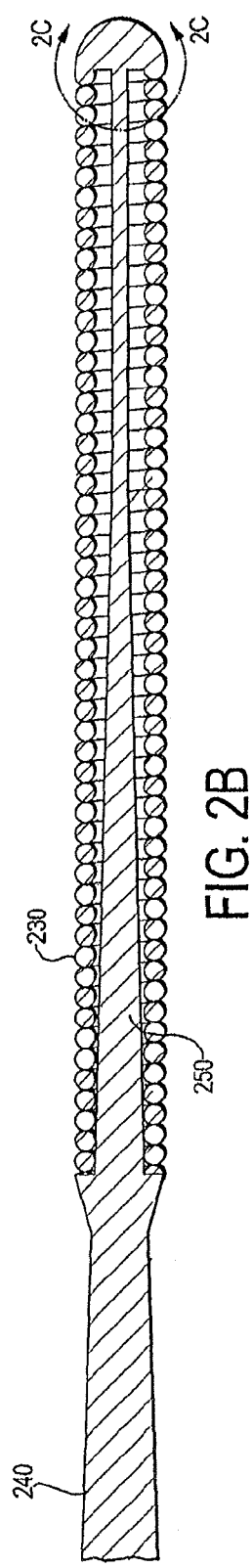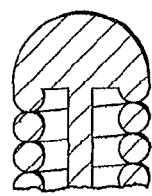

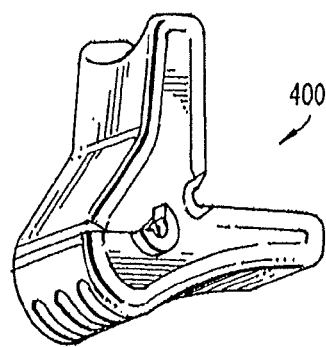
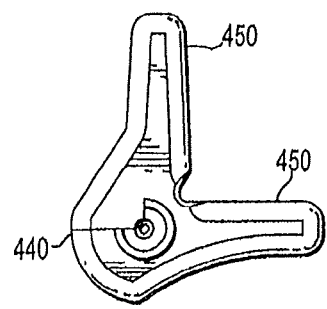
FIG. 4A  FIG. 4B
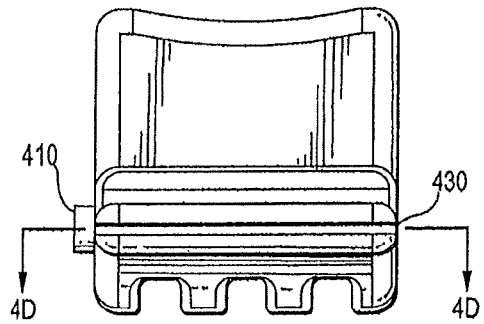
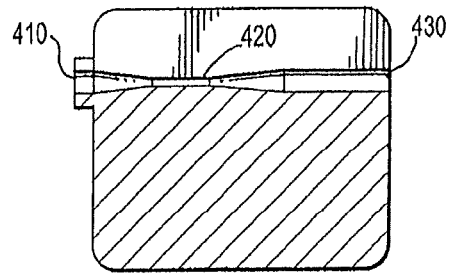
FIG. 4C  FIG. 4D
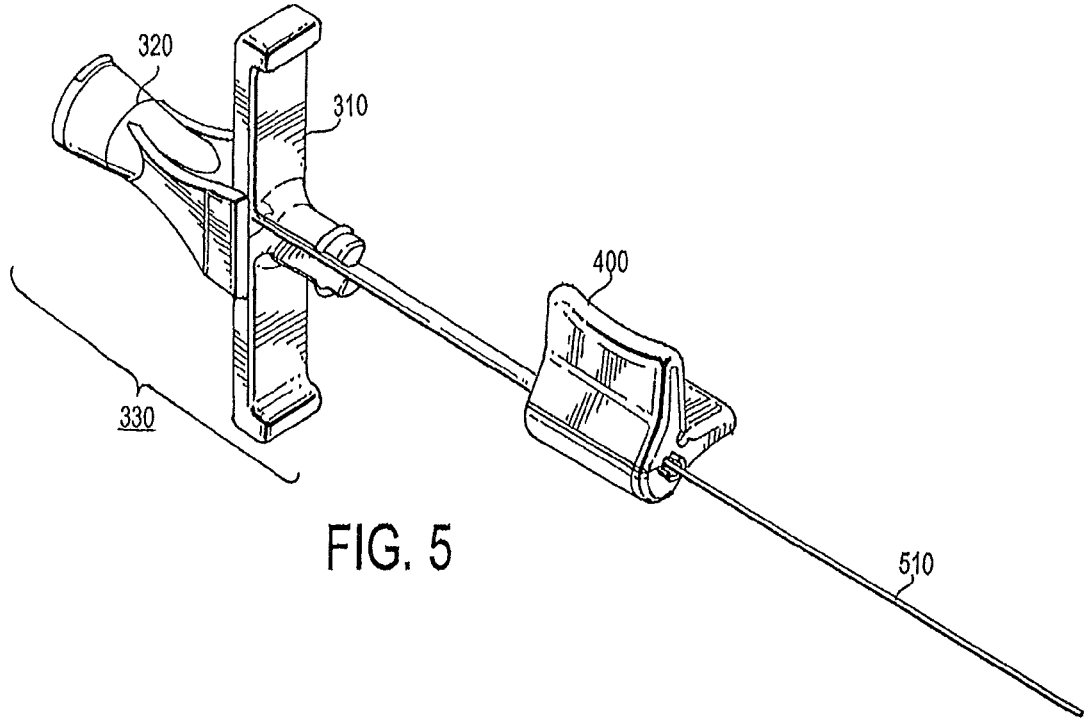
FIG. 5

GUIDEWIRE AND METHOD OF INSERTION OF SAME

RELATED APPLICATIONS

This application claims benefit of U.S. Provisional Application Ser. No. 61/226,428, filed Jul. 17, 2009, entitled "Guidewire and Method of Insertion of The Same," which application is incorporated herein by reference.

FIELD OF THE INVENTION

This invention relates to invasive medical devices which aid in the catheterization of human blood vessels, tracts, and cavities. In particular, this invention relates to a guidewire adapted for the catheterization of very small vasculature of the neonates, infants and children, an alignment adaptor that facilitates the catheterization of small vasculature utilizing said guidewire, and method of using the same.

BACKGROUND OF THE INVENTION

Catheterization of peripheral vasculature is performed generally using a method originally described by Seldinger or a modified Seldinger method.

According to the Seldinger method, an introducer needle is first inserted into a target vein. Bleeding from the needle indicated placement in the vessel. Alternatively, a syringe maybe attached to the needle (FIGS. 1A-1B). Aspiration of the syringe ensures proper placement of the needle within the vein. The syringe is then removed (FIGS. 1C-1D). A guidewire is fed through the introducer needle and into the target vein (FIG. 1E). The introducer needle is then removed, leaving the guidewire in the target vein (FIG. 1F). The guidewire is advanced until it reaches the desired location, e.g., the caval atrial junction. The proximal end of the guidewire is inserted into the distal tip of a catheter lumen. The catheter is fed into the target vein over the guidewire. The catheter is advanced along the guidewire until the distal tip is correctly positioned in the target vein. The guidewire is gently withdrawn. The catheter remains in the target vein.

According to the modified Seldinger method, after the advancement of the guidewire and removal of the introducer needle, a tear-away sheath/dilator assembly is threaded over the proximal end of the guidewire and into the target vein (FIGS. 1G-1H). The dilator is then removed from the sheath (FIG. 1I). The distal tip of catheter is inserted into and through the sheath until the catheter tip is correctly positioned in the target vein (FIG. 1J). The tear-away sheath is then removed by slowly pulling it out of the vessel while simultaneously splitting the sheath. The guidewire is gently withdrawn, leaving the catheter in the target vein (FIG. 1K). Alternatively, the guidewire is withdrawn with the dilator, and the catheter is inserted into the target vein through the sheath.

Catheterization may also be performed using the over-the-needle (OTN) method. According to this method, a tear-away sheath is placed directly exterior to the introducer needle. The tear-away sheath and the introducer needle are inserted simultaneously into the target vein. This method does not typically use a guidewire. A catheter is advanced into the target vein through the sheath.

For neonatal and pediatric applications, because the target vasculature is usually very small and tortuous, specially adapted devises are required to facilitate catheterization while minimizing the risk of vessel trauma. Existing types of small guidewire, typically are complex, and are only available such as neurovascular wires. There exists a need for a vascular guidewire specially adapted for the catheterization of small vasculature and other small tracts and cavities. There is a need for a miniature vascu-sheath and dilator specially adapted for the catheterization of small vasculature and other small tracts and cavities. There is also a need for a specially adapted alignment adaptor to facilitate the manipulation of such guidewire. Further, the specially adapted devices call for a novel method of use.

BRIEF DESCRIPTION OF THE DRAWINGS

The present invention will be better understood with reference to the following description taken in combination with the drawings. For the purpose of illustration, there are shown in the drawings certain embodiments of the present invention. In the drawings, like numerals indicate like elements throughout. It should be understood, however, that the invention is not limited to the precise arrangements, dimensions, and instruments shown. In the drawings:

FIG. 2A is a illustration of one embodiment of the present invention guidewire;

FIG. 2B is a cross-sectional view of the distal end of the guidewire shown in FIG. 2A;

FIG. 2C is a detailed view of the distal tip of the present invention guidewire as shown in FIG. 2B;

FIG. 4A is a perspective view of one embodiment of the present invention alignment adapter;

FIG. 4B is a top view of the alignment adapter shown in FIG. 4A;

FIG. 4C is a side view of the alignment adapter shown in FIG. 4A;

FIG. 4D is a cross-sectional view of the alignment adapter taken along line B-B in FIG. 4C; and FIG. 5 illustrates the positioning of a miniature vascular introducer assembly, an alignment adapter, and a guidewire at the step of threading of the guidewire into the miniature vascular introducer assembly.

DETAILED DESCRIPTION OF THE INVENTION

Figure 1:
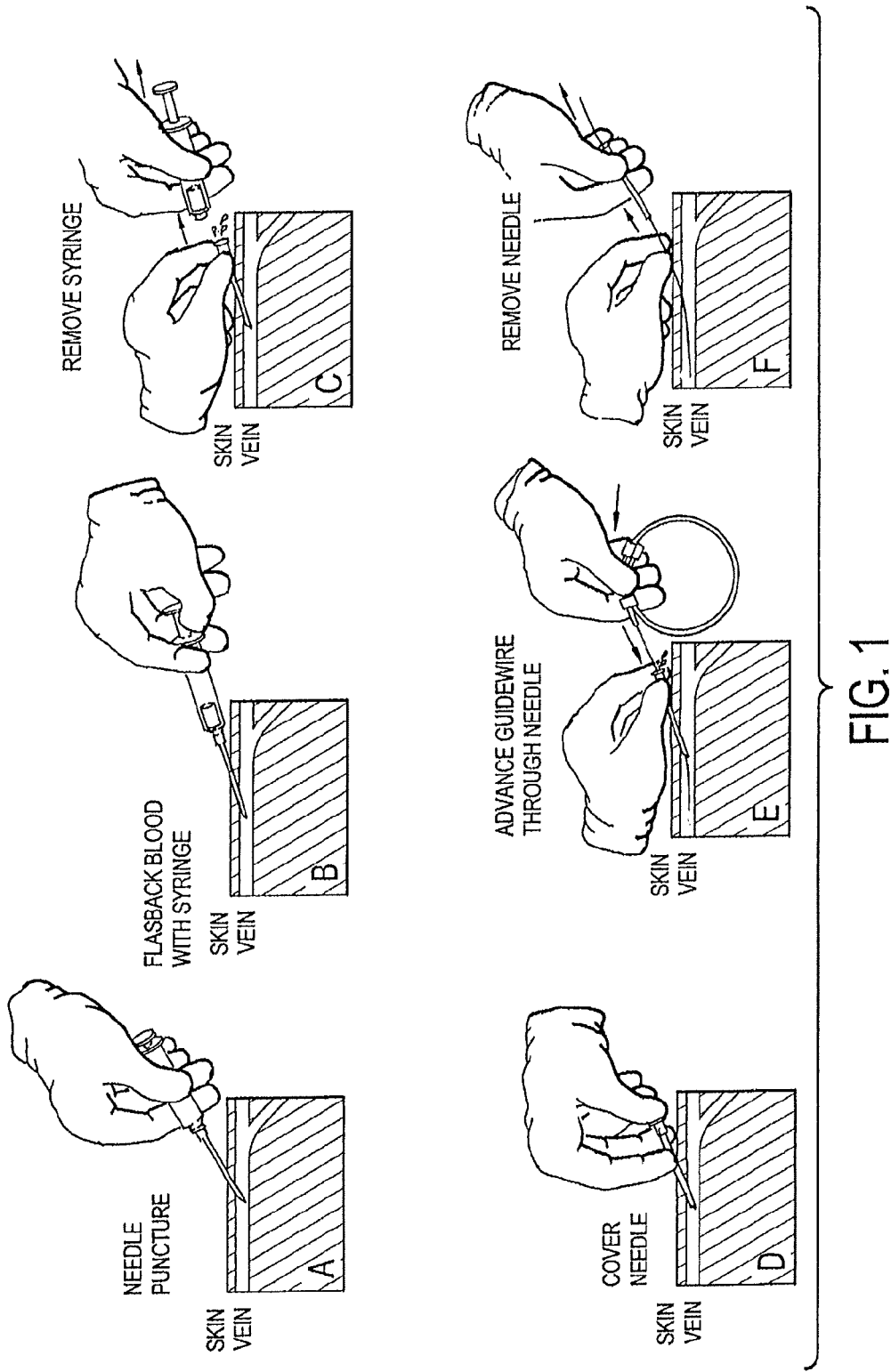
FIGS. 1A-1K is a illustration of the steps of modified Seldinger technique.

The words "proximal" and "distal" refer to directions away from and closer to, respectively, the insertion tip of a dilator to the present invention. The outer diameter of the dilator is expressed in terms of French size (Fr), which is defined as 1 Fr=⅓ mm.

Typical guidewires used for Central Venous Catheter (CVC) placement have diameters ranging between 0.018 and 0.038 inches. Smaller guidewires to 0.014 may also be used for CVC placement, however, these are typically designed/sold for peripheral interventions, coronary and other uses. These guidewires come in many different configurations.

The present invention provides a specially adapted thin guidewire for neonatal and pediatric applications. FIGS. 2A-2C illustrates one embodiment of the present invention guidewire 200. The design of the present invention guidewire as shown has several distinct features. The present invention guidewire 200 is generally of a smaller diameter than known vascular wires. The guidewire shown in the embodiment of FIGS. 2A-2C is a 0.010 inch diameter mandrel wire, which is significantly thinner. The shaft portion 210 of the present invention guidewire as shown in FIG. 2A a solid mandrel wire, typically made of surgical stainless steel. Materials other than stainless are commonly used, for example nitinol. In this particular embodiment, it is of a diameter of 0.010 inches. The present invention guidewire has a distal floppy tip 220. In this particular embodiment, the distal floppy tip 220 is formed by a grind section 250, located at the distal end of the shaft portion, and a coil 230 affixed over the grind section 250. The grind section 250 is generally of a conical shape, tapering from the proximal end to the distal end. The extreme distal end of the grind section 250 maybe flattened to control the stiffness of the floppy tip 220 (FIG. 2C). A flattened distal end provides additional strength. The coil 230 may be affixed to the grind section 250 by adhesive, solder, or welding, or any other suitable means. In this particular embodiment, the grind section 250 has a specific grind length in the range of 3-5 cm. This allows easier placement of the present invention guidewire through the peripheral vasculature and into the heart. Other particular tip designs may also be adapted to be used with the present invention guidewire.

The present invention also comprises a neck portion 240 between the distal floppy tip 220 and the shaft portion 210. This is typical in mandrel wire design where the shaft is ground forming a taper that decreases in diameter from proximal to distal and allows assembly of a floppy coil tip onto the shaft. In the embodiment shown in FIG. 2A, the guidewire 200 is constructed such that the coil section 230 is mated to the grind section 250 in such a way to strengthen the neck portion 240 of the guidewire just proximal to the distal floppy tip 220. This helps to prevent kinking of the guidewire proximal to the distal floppy tip. For larger guidewire kinking at the neck portion is not likely since the larger diameter of the shaft provides enough stiffness. However, for a thin guidewire as contemplated to be used in narrow and torturous vasculature, the kinking of the neck portion is a distinct risk factor the present invention is designed to address. Instead of a long grind section that extends past the coil as typically seen in larger guidewire, the embodiment illustrated in FIG. 2B has a shorter grind section 250, and additional shaft material deposited immediate proximal to the coil to provide the desired stiffness for the neck portion 240. By careful design, tolerance and assembly the diameter of the wire shaft just proximal to the coil is maximized to prevent kinking. In this particular embodiment, the grind section 250 has a specific grind length in the range of 3-5 cm. In the present invention the taper is shorter than typical and the tolerance of the coil and tapers are manipulated such that the diameter of the neck portion proximal to the taper is maximized. This allows easier placement of the present invention guidewire through the peripheral vasculature and into the heart.

Alternatively the neck portion may be reinforced by build-up of material in the neck region using a welding, soldering or adhesive process. Another embodiment would provide a shoulder where the coil abuts the mandrel shaft thereby reducing or eliminating the neck portion. Yet another alternative would use flat wire for formation of the tip so as to increase the diameter of the tapered section of wire and thus provide more rigidity in the neck region.

Additionally, the present invention guidewire 200 may be coated with a variety of readily available coatings. The coatings can provide additional slipperiness to the guidewire and further facilitate the insertion of the guidewire.

Figure 3A:
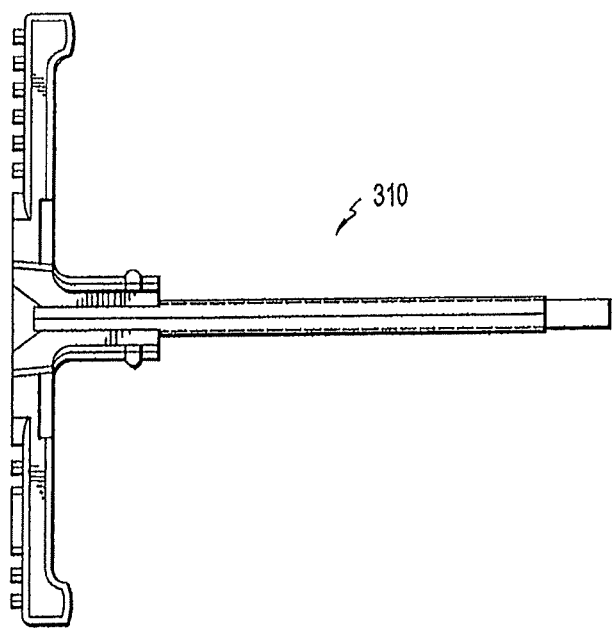
FIG. 3A is a side view of a representative example of a miniature tear-away vascular introducer sheath.
Figure 3B:
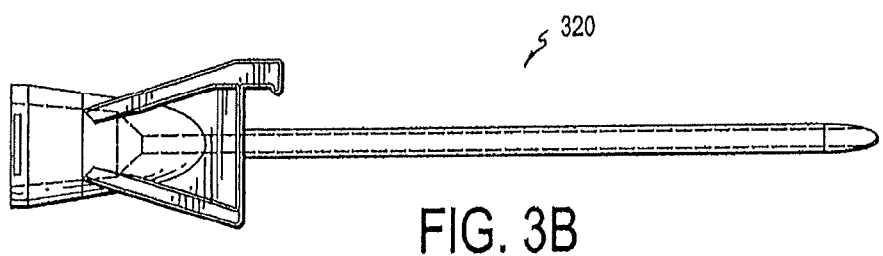
FIG. 3B is a side view of a representative example of a miniature dilator.
Figure 3C:
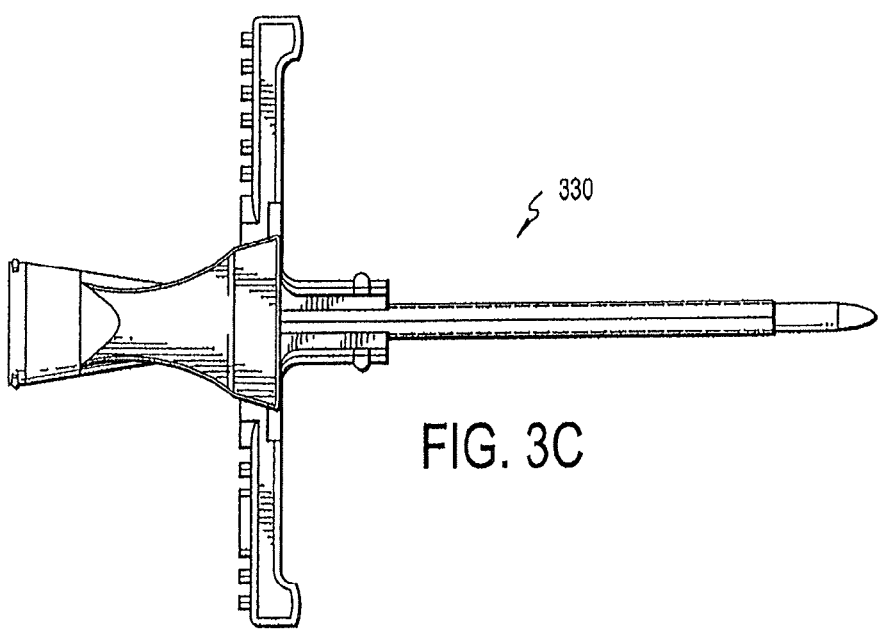
FIG. 3C is a side view of a representative example of a miniature vascular introducer assembly comprising the miniature tear-away vascular introducer sheath of FIG. 3A and the miniature dilator of FIG. 3B.

Neonatal and pediatric catheterization requires specially adapted vascular introducer. A miniature vascu-sheath has been devised specifically for the insertion procedure. An example of miniature vascular introducer is illustrated in FIGS. 3A-3C. A miniature vascular introducer 330 generally comprises of a dilator 320 and a vascular sheath 310. A dilator 320 generally has a long shaft portion and a proximal hub. The shaft portion of the dilator usually has a tapered tip on its distal end. The dilator also has a hollow center, which runs along the entire length of the dilator. The center channel forms a passage for the guidewire to pass through the center of the dilator. A vascular sheath 310 has a long thin walled tubular portion and a sheath hub. The tubular portion of the sheath has a slightly tapered distal end and an internal diameter slightly larger than the outer diameter of the dilator. The sheath fits outside of the dilator and forms a continuous outer surface.

In the particular embodiment of miniature vascu-sheath shown in FIG. 3A, tear-away seams are introduced along the midline of the vascu-sheath. The vascu-sheath can be split along the tear-away seam by pulling the tabs in opposite directions. An information area is formed on the top surface of the at least one of the tabs. Information relevant to the use of the vascu-sheath, such as size information can be indicated in the information area. Numbers of lettering can be prominently displayed in the information area by methods such as stamping, hot stamping, or printing, or directly molded on the vascu-sheath tabs.

A latching mechanism is introduced to secure the dilator to the vascu-sheath. In the particular embodiment of miniature dilator shown in FIG. 3A, the latching mechanism is a substantially flat piece extending from one side of the base of the dilator hub. The flat piece having a raised distal edge that mates with a recess or grove in the corresponding vascu-sheath hub, thus securing the dilator to the vascu-sheath. Other mechanism of securing the dilator with the vascu-sheath may also be used.

Thin guidewire and miniature vascular introducer used in neonatal and pediatric applications are particularly difficult to handle. During the catheterization procedure, after the vein has been accessed, the clinician needs to thread the dilator and the vascu-sheath over the proximal shaft of the guidewire. Typical guidewire used for peripherally inserted central venous catheters (PICCs) are 0.018 inches in diameter or larger. These are small, but generally not too difficult to work with. This difficulty in handling is rarely a problem in conventional catheterization. However, the size of the thin guidewire and miniature vascu-sheath/dilator assemblies used in the neonatal and pediatric applications makes threading the miniature vascu-sheath/dilator assemblies over the thin guidewire difficult. This can be extremely difficult since the inside diameter (ID) of the dilator tip closely matches the guidewire outside diameter (OD). An alignment adaptor has been designed to facilitate the threading of the vascu-sheath/dilator assembly over the present invention guidewire.

FIGS. 4A-4D illustrate one embodiment of the alignment adaptor 400. The alignment adaptor having openings at both the proximal end 410 and the distal end 430. The proximal end opening 410 is designed to accept the distal end of the vascu-sheath/dilator assembly. The distal end opening 430 is designed to accept the proximal end of the guidewire shaft. A center channel 420 connects the proximal opening 430 and the distal opening 410. The central channel 420 has a diameter slightly larger than the diameter of the guidewire. The proximal end opening 410 and the distal end opening 430 having relative large mouth and gradually narrow to connect with the central channel 420. The alignment of the proximal opening 430, the center channel 420, and the distal opening 410 ensures that when the guidewire passes through the distal opening 410 and exits from the center channel 420, it is positioned at the center of the proximal opening 430, which coincides with the center of the distal opening of the dilator tip. A slit 440 is introduced along one side of the longitudinal axis of the alignment adaptor. Tabs 450 maybe formed on both sides of the slit. Forces can be applied to the tabs 450 to open up the slit 440, providing an exit path for the guidewire once it is properly threaded through the vascu-sheath/dilator assembly.

The alignment adaptor as shown in FIGS. 4A-4D uses a soft thermoplastic elastomer material suitable for medical applications. It is approximately 50 A durometer. The material softness provides two advantages: 1.) a single molding rod with complex shape, such as funneled on both ends, can be used for molding and then removed from the part (due to its elasticity) without complex & expensive tooling features; 2.) the soft material allows the part to flex and thereby open when the wings are pinched—this for easy removal from the wire. These same features can be implemented with similarly soft materials such as silicone or urethanes. Durometers for such suitable materials would likely vary from 15 A to 100 A.

Alternative designs for the adaptor may include a relatively rigid body, where the distal opening, center channel, and proximal opening are located, with a living hinge or similarly designed thin section. A slit similar to the one in the embodiment shown in FIGS. 4A-4D is formed opposite to the hinge or thin section. Wings are introduced on both sides of the hinge or thin section. The hinge or thin section allows the body to flex and open when the wings are pinched. This alternative embodiment can be made from polypropylene, polyethylene, nylon, urethane or similar materials.

Another alternative design could also be a splittable alignment adaptor that can be peeled from the dilator after insertion of the guidewire into the vascu-sheath. In this design, no slit is needed to be introduced in the formation of the alignment adapter.

A further alternative design for the alignment adaptor involves a two-piece body part that is snapped together or temporarily bonded. The body part can then be broken in two for removal.

An additional alternative design may encompass a simple split tube that after assembly of the vascu-sheath onto the guidewire is peeled off of the part—a handle attachment on the tube could be incorporated to help remove it from the part.

When using the alignment adaptor 400 as shown in FIGS. 4A-4D, the vascu-sheath/dilator assembly is positioned in the proximal opening of the alignment adaptor. The alignment adaptor can be placed on the dilator tip by the clinician which provides a opening for feeding the guidewire into the dilator. The alignment adaptor may also be positioned on the distal tip of the vascu-sheath/dilator assembly at the time of packaging.

FIG. 5 illustrates the positioning of a miniature vascular introducer assembly 330, an alignment adapter 400, and a guidewire 510 at the step of threading of the miniature vascular introducer assembly 330 over the guidewire 510. At this step, the guidewire is placed in the patient, possibly to a specific position within the vasculature by a clinician. The proximal opening 430 of the alignment adaptor 400 is placed atop the distal end of the miniature vascular introducer assembly. The clinician then aligns the distal opening 410 of the alignment adaptor 400 with the proximal end of the guidewire 510. The alignment adaptor 400 and the miniature vascular introducer assembly 330 is slid over the guidewire 510. The guidewire 510 passes through the center channel 420 into the lumen of the dilator 320. Since the distal opening 410 provides an entry point significantly larger than the distal opening of the dilator, threading an alignment adaptor over a guidewire is much easier than threading a dilator directly over a guidewire without aid. The distal opening 410 is centrally aligned with the center channel 420 and the proximal opening 430. Once the guidewire 510 enters into the distal opening 410, the alignment adaptor 400 and the miniature vascular introducer assembly 330 slide along the guidewire 510, which ensures the guidewire 510 is centered to the dilator lumen once it exits the central channel 420. This advantage is apparent when the guidewire and the dilator are of small sizes, such as the ones used in neonatal and pediatric applications. The present invention alignment adaptor provides a clinician the ease and confidence to thread a miniature vascu-sheath/dilator assembly over a thin guidewire in one simple step. After the miniature vascular introducer assembly 330 is successfully placed over the guidewire 510, the adaptor is unclipped from both the miniature vascular introducer assembly 330 and guidewire 510 and removed. The miniature vascular introducer assembly 330 can then be inserted into the target vein along the guidewire 510.

Procedures for modified Seldinger or Seldinger insertion of very small catheters into peripheral vasculature of neonates, infants and children are adapted using the present invention guidewire and alignment adaptor.

The procedure for insertion entails access into the vasculature, placement of the present invention guidewire, e.g., 0.010 guidewire, placement of a miniature tear-away introducer (vascu-sheath) followed by placement of the catheter and removal of the sheath. Alternatively, the catheter might be placed directly over the wire into the vasculature without using the aid of the vascu-sheath. In that instance, a very small dilator might be used and the skin might be nicked using a scalpel.

Access into the vasculature for this procedure will be performed using the smallest possible needle that allows passage of the guidewire. For a 0.010 guidewire, approximately 26 ga or larger. Initial access may also be performed using an AngioCath™ type IV catheter (manufactured by Becton Dickson) since this is device end-users are accustomed to using. Either method allows for access into the peripheral or central venous system using a much less traumatic method than the standard of practice. Currently, vein access for placement of a 1.9 F catheter uses a 2 F over-the-needle (OTN) device that employs a 22 ga needle. A 22 ga needle has a diameter of 0.028 inches. A 2.6 F or 3 F catheter uses a 3 F OTN that employs a 19 ga needle. A 19 ga needle has a diameter of 0.042 inches. A 26 ga needle has a diameter of 0.018 inches, less than half that of the 19 ga. Clearly this is preferential. It provides a much less traumatic access method, especially in neonates where the veins are extremely small.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:

1. An alignment adaptor for facilitating the insertion of a guidewire into a dilator, comprising:
   a distal opening for receiving a proximal end of a guidewire;
   a proximal opening for receiving a distal end of a dilator;

a center channel connecting the distal opening to the proximal opening, the center channel comprising a first longitudinal side, a second longitudinal side, and a longitudinal, planar opening extending along the first longitudinal side from the distal opening to the proximal opening; and a first tab and a second tab disposed on either side of the longitudinal, planar opening to open the longitudinal, planar opening when forces are applied to the first and second tabs, wherein the distal opening, the center channel, and the proximal opening are centrally aligned, wherein the first and second tabs are perpendicular to one another, wherein the first tab is parallel to the longitudinal, planar opening, wherein the second tab is perpendicular to the longitudinal, planar opening, and wherein the center channel is configured to flex along the second longitudinal side to open the longitudinal, planar opening to permit removal of the guidewire through the longitudinal, planar opening when forces are applied to the first and second tabs.

2. The alignment adaptor of claim 1, wherein the longitudinal, planar opening is a planar slit extending along the first longitudinal side of the channel from the distal opening to the proximal opening.

3. The alignment adaptor of claim 1, wherein the longitudinal, planar opening is configured allow lateral exit of the guidewire when the longitudinal, planar opening is opened.

4. An alignment adaptor for facilitating the insertion of a guidewire into a dilator, comprising:

a distal opening for receiving a proximal end of a guidewire;

a proximal opening for receiving a distal end of a dilator;

a center channel connecting the distal opening to the proximal opening, the center channel comprising a first longitudinal side, a second longitudinal side opposite the first longitudinal side, and a single, planar slit extending along the first longitudinal side from the distal opening to the proximal opening; and a first tab and a second tab positioned on each side of the single, planar slit to open the single, planar slit when forces are applied to the first and second tabs, wherein the distal opening, the center channel, and the proximal opening are centrally aligned, wherein the alignment adaptor is formed as a single unit, wherein the first and second tabs are perpendicular to one another, wherein the first tab is parallel to the single, planar slit, wherein the second tab is perpendicular to the single, planar slit, and wherein the center channel is configured to flex along the second longitudinal side of the center channel to open the single, planar slit to permit removal of the guidewire through the single, planar slit when forces are applied to the first and second tabs.

5. The alignment adaptor of claim 4, wherein the alignment adaptor is made of a soft thermoplastic elastomer material suitable for medical applications.

6. The alignment adaptor of claim 5, wherein the soft thermoplastic elastomer material is silicone.

7. The alignment adaptor of claim 5, wherein the soft thermoplastic elastomer material is urethane.

8. The alignment adaptor of claim 5, wherein the soft thermoplastic elastomer material has a durometer from 15 A to 100 A.

9. The alignment adaptor of claim 8, wherein the soft thermoplastic elastomer material has a durometer of approximately 50 A.

10. A method of threading a guidewire through a dilator, the guidewire comprising proximal and distal ends, the dilator comprising a proximal end, a distal end, and a central lumen, the method comprising steps of:

positioning the distal end of the dilator in an alignment adaptor according to claim 4;

placing the distal opening of the alignment adaptor over the proximal end of the guidewire;

sliding the alignment adaptor and the dilator over the guidewire, wherein the guidewire passes through the central channel of the alignment adaptor into the central lumen of the dilator;

applying force to the first and second tabs of the alignment adaptor to cause the center channel of the alignment adaptor to flex along the second longitudinal side of the center channel and to cause the single, planar slit to open; and removing the guidewire and the dilator from the alignment adaptor by sliding the guidewire and the dilator through the opened single, planar slit.

* * * * *